(12) United States Patent
Hsieh et al.

(10) Patent No.: US 12,329,444 B2
(45) Date of Patent: Jun. 17, 2025

(54) TISSUE IMAGING METHOD

(71) Applicant: Industrial Technology Research Institute, Hsinchu (TW)

(72) Inventors: Wan-Hsin Hsieh, Taoyuan (TW); Yu-Yao Wang, Taoyuan (TW); Zong-Yi Hsiao, Nantou County (TW); Hui-Hsin Lu, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 629 days.

(21) Appl. No.: 17/089,726

(22) Filed: Nov. 5, 2020

(65) Prior Publication Data

US 2021/0128234 A1 May 6, 2021

Related U.S. Application Data

(60) Provisional application No. 62/930,583, filed on Nov. 5, 2019.

(30) Foreign Application Priority Data

Sep. 16, 2020 (TW) .................................. 109131879

(51) Int. Cl.
*A61B 18/14* (2006.01)
*A61B 18/00* (2006.01)
*A61B 90/00* (2016.01)

(52) U.S. Cl.
CPC .......... *A61B 18/1492* (2013.01); *A61B 90/36* (2016.02); *A61B 2018/0019* (2013.01);
(Continued)

(58) Field of Classification Search
CPC .. A61B 2018/0019; A61B 2018/00982; A61B 2018/00994; A61B 2018/00577;
(Continued)

(56) References Cited

U.S. PATENT DOCUMENTS 7,601,122 B2   10/2009  Zagzebski et al.
8,328,726 B2   12/2012  Varghese et al.
(Continued)

FOREIGN PATENT DOCUMENTS

CN   101779966   7/2010
CN   109859833   6/2019
(Continued)

OTHER PUBLICATIONS

"Office Action of Taiwan Counterpart Application", issued on Apr. 20, 2021, p. 1-p. 3.
(Continued)

*Primary Examiner* — Khadijeh A Vahdat
*Assistant Examiner* — Marina Delaney Templeton
(74) *Attorney, Agent, or Firm* — JCIPRNET (57) ABSTRACT

The present disclosure provides a tissue imaging method, including: inserting an electronic probe into a lesion area of a patient and ablating tissue of the lesion area; capturing a first image including the lesion area by using an imaging apparatus; vibrating the electronic probe to generate displacement of at least a portion of the tissue of the lesion area, and capturing a second image including the lesion area by using the imaging apparatus; generating a correlation image according to a correlation between the first image and the second image; and computing an ablation boundary according to the correlation image.

8 Claims, 8 Drawing Sheets

(52) U.S. Cl.
CPC .............. *A61B 2018/00577* (2013.01); *A61B 2018/00982* (2013.01); *A61B 2018/00994* (2013.01); *A61B 2090/364* (2016.02)

(58) Field of Classification Search
CPC .......... A61B 2018/00738; A61B 90/36; A61B 90/37; A61B 90/361; A61B 2090/364; A61B 2090/061; A61B 2090/067; A61B 2090/373; A61B 2090/374; A61B 2090/376; A61B 2090/3762; A61B 2090/378; A61B 18/1492; A61B 18/14; A61B 18/1477; A61B 8/485; A61B 8/4245; A61B 8/483; A61B 8/488; A61B 8/0883; A61B 8/5246; A61B 5/055; A61B 5/0051; A61B 5/0066; A61B 5/02007; A61B 5/0035; A61B 5/02133; A61B 2034/107; A61B 34/10; A61B 2017/00106; A61B 17/320068; A61B 17/22004; G06T 7/0012; G06T 2207/10132; G06T 2207/10088; G06T 2210/41; A61N 7/00; A61N 2007/0078; A61N 2007/0026; A61N 2007/0052
See application file for complete search history.

(56) References Cited

U.S. PATENT DOCUMENTS

| | | | | |
|---|---|---|---|---|
| 8,545,407 | B2* | 10/2013 | Bercoff | G01N 29/36 600/407 |
| 8,556,888 | B2 | 10/2013 | Nields et al. | |
| 9,715,885 | B2 | 7/2017 | Sugiyama et al. | |
| 9,913,624 | B2 | 3/2018 | Varghese et al. | |
| 10,241,028 | B2 | 3/2019 | Rowe et al. | |
| 10,488,247 | B2* | 11/2019 | Varghese | A61B 8/485 |
| 2003/0171672 | A1* | 9/2003 | Varghese | A61B 5/015 600/420 |
| 2008/0287780 | A1* | 11/2008 | Chase | A61B 5/0091 600/425 |
| 2010/0256530 | A1* | 10/2010 | Varghese | A61B 18/18 600/587 |
| 2010/0268225 | A1 | 10/2010 | Coe et al. | |
| 2014/0046316 | A1* | 2/2014 | Ladtkow | A61B 6/487 606/33 |
| 2014/0112566 | A1 | 4/2014 | Steinberg et al. | |
| 2015/0327837 | A1 | 11/2015 | Qi et al. | |
| 2017/0319159 | A1* | 11/2017 | Tian | A61B 6/48 |
| 2018/0008237 | A1* | 1/2018 | Venkataraman | A61B 8/4263 |
| 2018/0168537 | A1 | 6/2018 | Hsieh et al. | |
| 2019/0142528 | A1 | 5/2019 | Vertikov | |

FOREIGN PATENT DOCUMENTS

| | | |
|---|---|---|
| TW | I463964 | 12/2014 |
| TW | I498099 | 9/2015 |
| WO | 03075771 | 9/2003 |
| WO | 2016115031 | 7/2016 |

OTHER PUBLICATIONS

T. Varghese et al., "Elastographic Imaging of Thermal Lesions in the Liver in Vivo Following Radiofrequency Ablation: Preliminary Results", Ultrasound in Medicine & Biology, Jan. 2002, pp. 1467-1473.

Jingjing Xia et al., "Considering Angle Selection When Using Ultrasound Electrode Displacement Elastography to Evaluate Radiofrequency Ablation of Tissues" BioMed Research International, May 2014, pp. 1-11.

Shyam Bharat et al., "Radio-frequency ablation electrode displacement elastography: A phantom study", Medical Physic, Jun. 2008, pp. 2432-2442.

* cited by examiner

TISSUE IMAGING METHOD

CROSS-REFERENCE TO RELATED APPLICATION

This application claims the priority benefit of U.S. application Ser. No. 62/930,583, filed on Nov. 5, 2019, the disclosure of which is incorporated by reference herein in its entirety, and claims the benefit of Taiwan application Serial No. 109131879, filed Sep. 16, 2020, the subject matter of which is incorporated herein by reference.

TECHNICAL FIELD

The disclosure relates to a tissue imaging method, and particularly relates to a tissue imaging method that judges from the images before and after vibration of an ablation area whether or not an ablation is complete.

BACKGROUND

Radiofrequency ablation (RFA) has gradually become a clinical treatment for stage I and II liver tumors. The treatment requires confirmation of complete ablation of the tumor area. If the tumor area is not completely ablated, the tumor will recur in situ, in which the one-year recurrence rate is about 29%. In recent years, hospitals have gradually initiated clinical trials using ultrasound developers to confirm the ablation effect. In the procedure of confirming ablation, a single-use electronic probe will be withdrawn from the human body first, and the developer is then injected after 15 minutes for imaging, so as to confirm whether or not the lesion area is completely ablated. If there is an area with incomplete ablation, electronic probe puncture and ablation will be performed again. Approximately 5% of patients are allergic to developer, and the developer cannot be used to confirm the ablation range. Moreover, the cost of the developer and the doctor's operation fee add to the patient's financial burden. If the patient needs another puncture and ablation, payment for another electronic probe will occur, increasing the cost of the operation. Therefore, how to more efficiently confirm whether or not the lesion area is completely ablated is the goal that those skilled in the art should strive for.

SUMMARY

The disclosure provides a tissue imaging method, including: inserting an electronic probe into a lesion area of a patient to ablate tissue of the lesion area; capturing a first image including the lesion area by using an imaging apparatus; vibrating the electronic probe to generate displacement of at least a portion of the tissue of the lesion area, and capturing a second image, including the lesion area when the electronic probe vibrates, by using the imaging apparatus; generating a correlation image according to a correlation between the first image and the second image; and computing an ablation boundary according to the correlation image.

In summary, in the tissue imaging method of the disclosure, an electronic probe is inserted into the lesion area of the patient to ablate the tissue of the lesion area, and the first image including the lesion area, and the second image, including the lesion area when the electronic probe vibrates, are captured by using the imaging apparatus. After computing the correlation between the first image and the second image to generate the correlation image, the ablation boundary according to the correlation image may be computed to confirm whether or not the lesion area is completely ablated.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF DISCLOSED EMBODIMENTS

Reference will now be made in detail to the exemplary embodiments of the disclosure, examples of which are illustrated in the accompanying drawings. Wherever possible, the same reference numbers are used in the drawings and the description to refer to the same or like parts.

The disclosure provides a tissue imaging method capable of efficiently judging from images before and after vibrating of an ablation area whether or not a lesion area is ablated completely.

Figure 1:
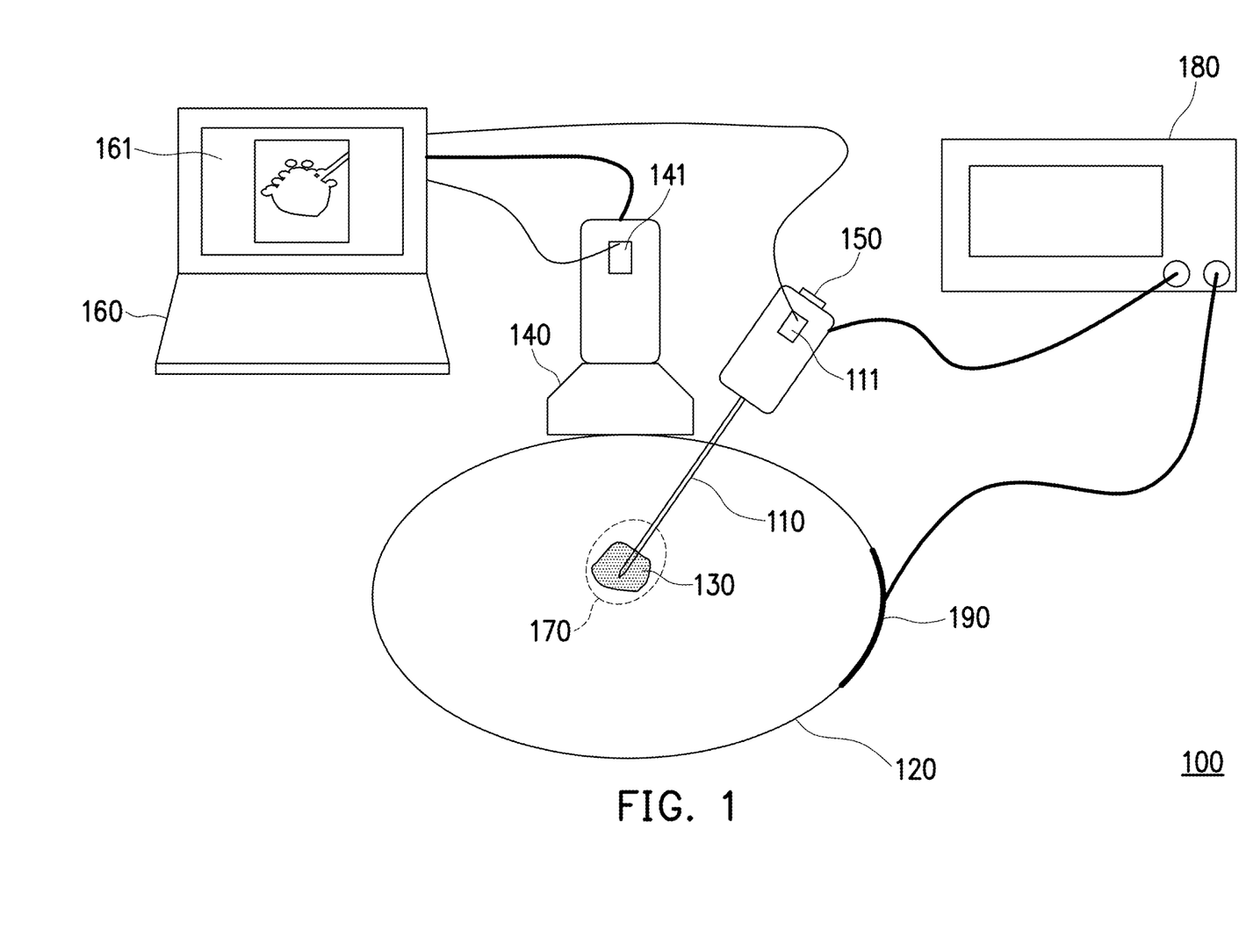
FIG. 1 is a schematic diagram illustrating a tissue imaging system according to an exemplary embodiment.

FIG. 1 is a schematic diagram illustrating a tissue imaging system according to an exemplary embodiment.

Please refer to FIG. 1. When a doctor performs an ablation operation, using a tissue imaging system 100, the doctor may insert an electronic probe 110 into a lesion area 130 of a patient 120 and ablate tissue of the lesion area 130. After the ablation is completed, an imaging apparatus 140 may capture a first image including the lesion area 130. Then, the doctor may activate an actuator 150 to vibrate the electronic probe 110 so as to generate displacement of at least a portion of the tissue of the lesion area 130, and capture a second image including the lesion area 130 by using the imaging apparatus 140. The imaging apparatus 140 may transmit the first image and the second image to an electronic device 160. The electronic device 160 may generate a correlation image according to a correlation between the first image and the second image, and compute an ablation boundary 170 according to on the correlation image. The correlation image and the ablation boundary 170 may be displayed on a screen 161 of the electronic device 160 for the doctor to judge whether or not the ablation is complete. The electronic probe 110 may be coupled to the electronic device 160 and a high frequency host 180, and the high frequency host 180 may be coupled to a loop electrode 190 contacting the patient 120.

The imaging apparatus 140 may be, for example, an ultrasonic device, a computed tomography (CT) device, a magnetic resonance imaging (MRI) device, or an X-ray device. The electronic device 160 may be, for example, a personal computer, a notebook computer, or other computers and the like. It should be noted that the electronic probe 110 and the imaging apparatus 140 may include a sensor 111 and a sensor 141, configured to detect a distance and/or an angle difference between the electronic probe 110 and the imaging apparatus 140. The sensor 111 and the sensor 141 may be, for example, an inertial sensor, an optical sensor, an electromagnetic induction sensor or a stereo vision sensor, or the like. The disclosure does not limit the types of the sensor 111 and the sensor 141.

Figure 2:
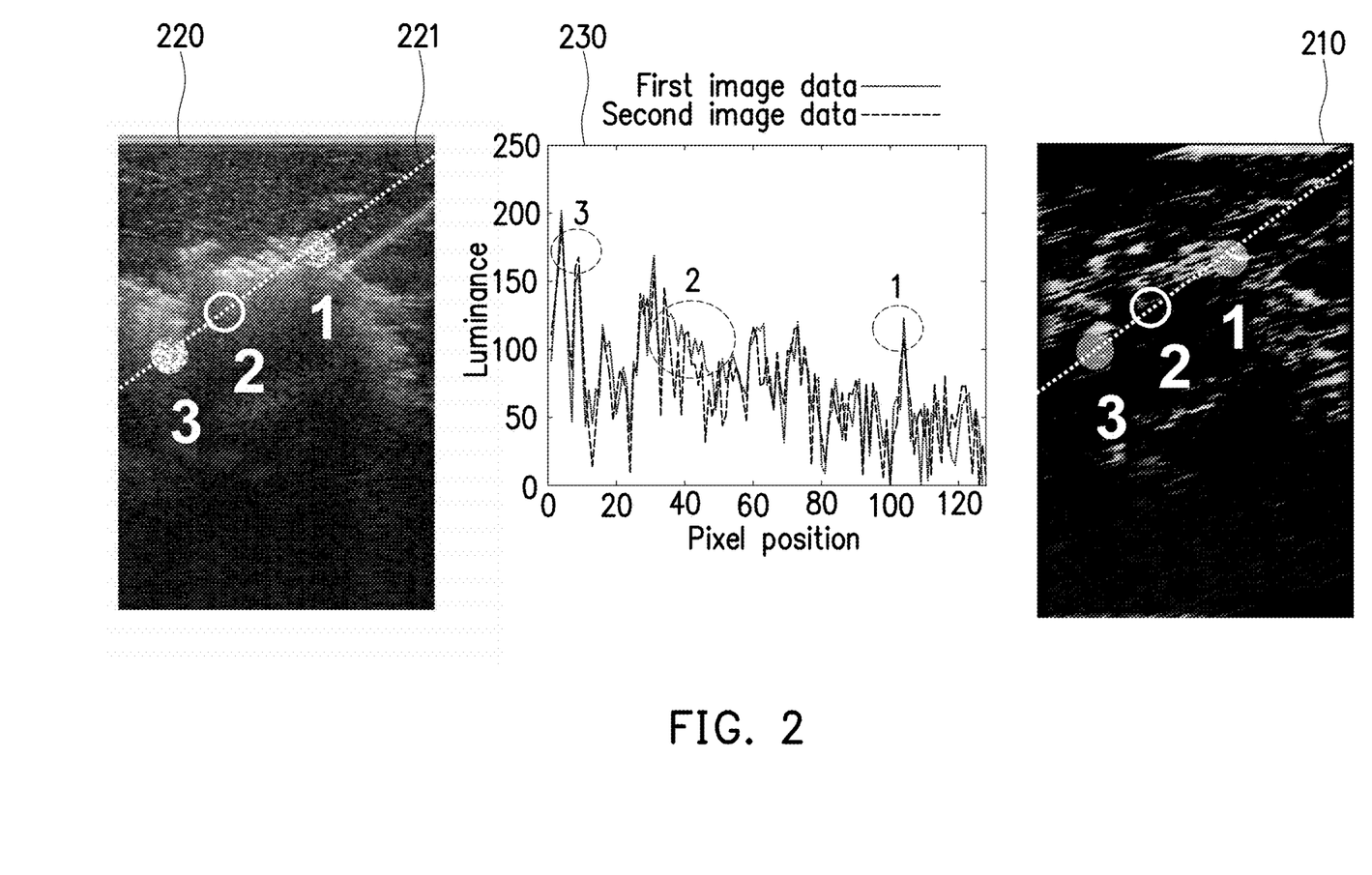
FIG. 2 is a schematic diagram illustrating a correlation image according to an exemplary embodiment.

FIG. 2 is a schematic diagram illustrating a correlation image according to an exemplary embodiment.

Please refer to FIG. 1 and FIG. 2. The electronic device 160 may generate a correlation image 210 according to a correlation between the first image and the second image. In detail, a pixel value of each pixel in the correlation image 210 represents the correlation between a corresponding pixel in the first image and a corresponding pixel in the second image. In other words, when a luminance difference between the corresponding pixel in the first image and the corresponding pixel in the second image of a pixel is smaller, the pixel has a larger pixel value in the correlation image 210. Taking a captured image 220 as the second image, for example. The captured image 220 may include three points such as point "1", point "2", and point "3". The point "1" and the point "3" are located at a periphery of an ablation area where soft tissue is not hardened, therefore the soft tissue may absorb the micro-vibration of the electronic probe 110 without displacement/deformation, such that the image data before and after the vibration (i.e. the first image and the second image) have a high degree of correlation, represented by a pixel with higher luminance in the correlation image 210. The point "2" is located at an edge of the ablation area where the soft tissue has hardened; therefore, the hardened tissue absorbs the micro-vibration of the electronic probe 110 and generates displacement/deformation, such that the degree of correlation of the image data before and after the vibration (i.e. the first image and the second image) is decreased, represented by a pixel with lower luminance in the correlation image 210. In a pixel luminance map 230, a horizontal axis represents pixel positions arranged along a dotted line 221 and a vertical axis represents pixel luminance.

Figure 3:
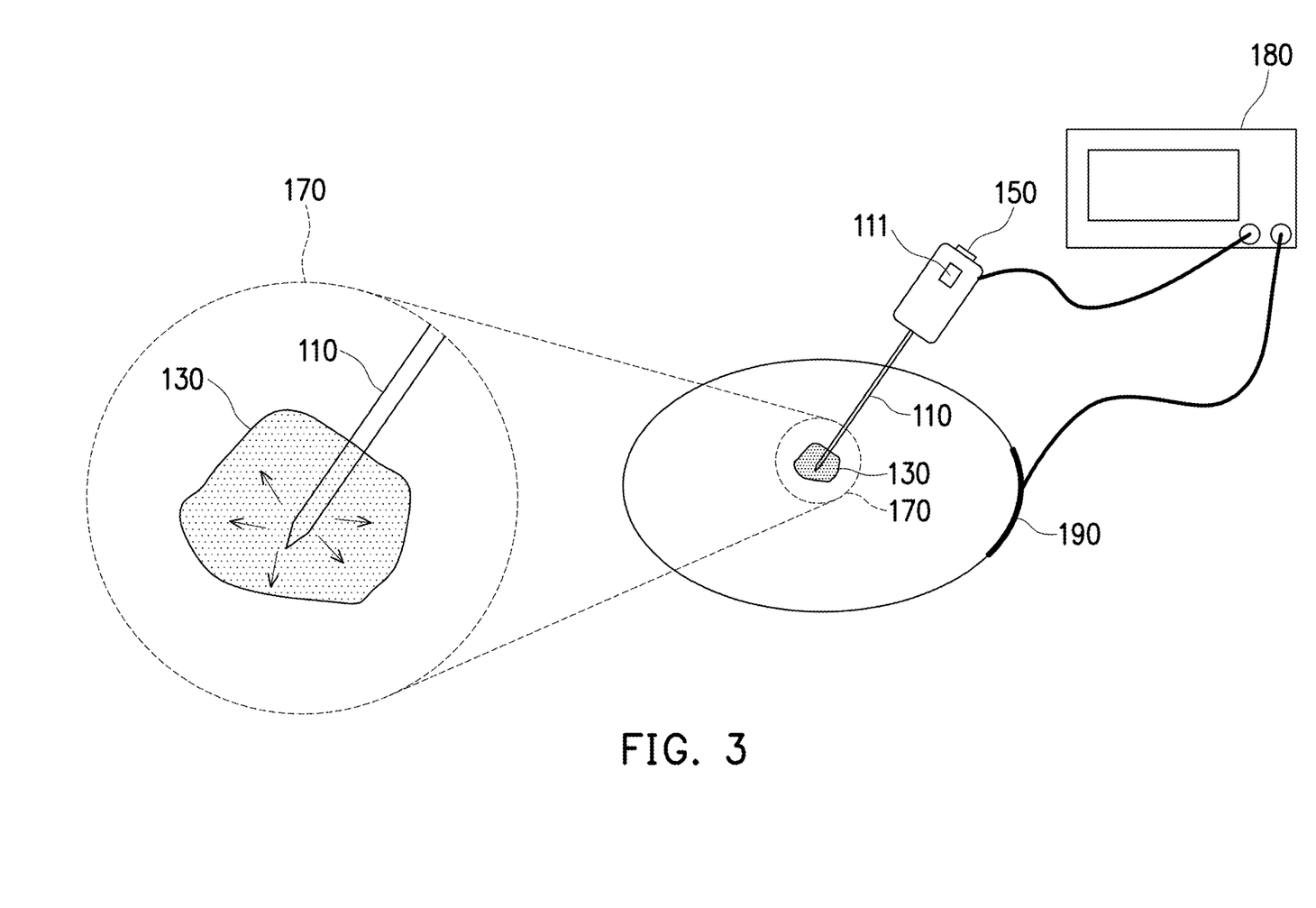
FIG. 3 is a schematic diagram illustrating a vibrating electronic probe according to an exemplary embodiment.

FIG. 3 is a schematic diagram illustrating a vibrating electronic probe according to an exemplary embodiment.

Please refer to FIG. 1 and FIG. 3. The electronic probe 110 may vibrate in multiple directions from a static initial position, and an angle of the multi-directional vibration may be larger than an angle threshold value (for example, 180 degrees) to obtain a correlation image that may determine the ablation boundary. In detail, the electronic probe 110 may vibrate in at least a first direction and a second direction from the initial position, and an angle value between a first vector corresponding to the first direction and a second vector corresponding to the second direction is larger than the angle threshold value.

Figure 4:
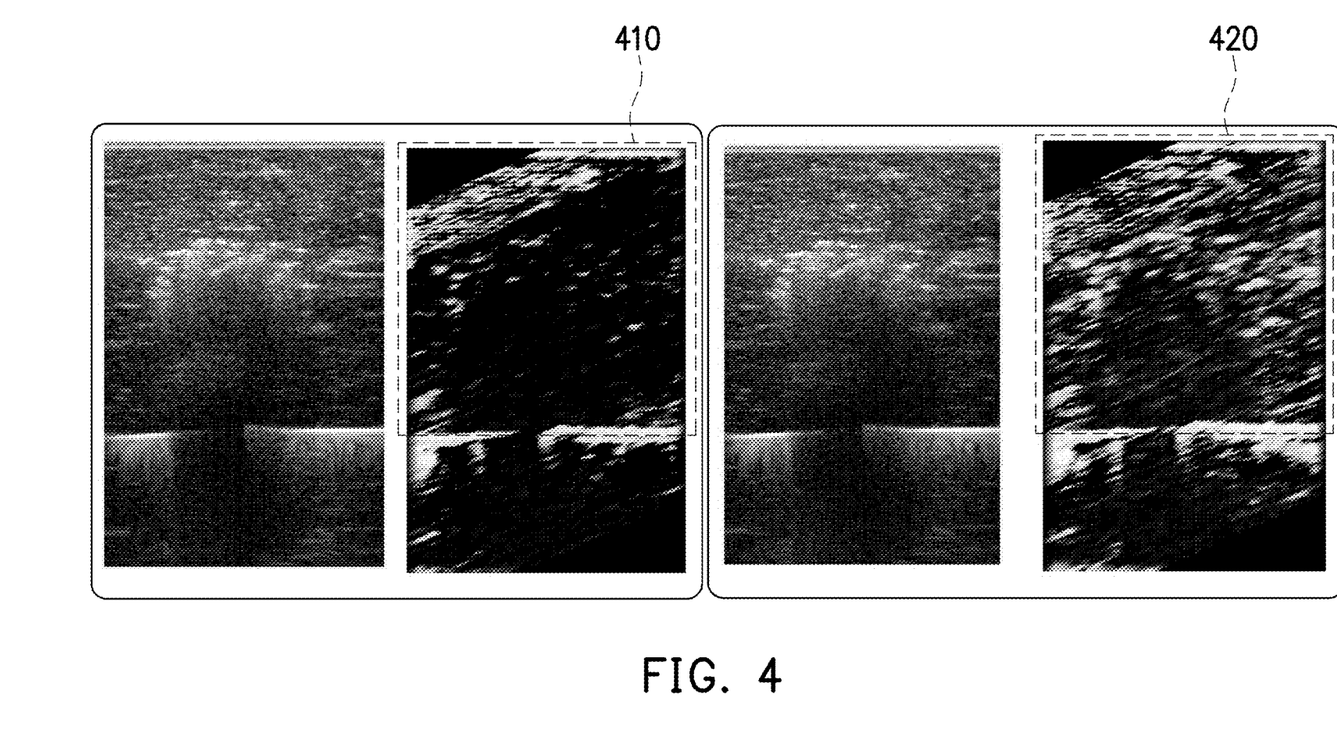
FIG. 4 is a schematic diagram illustrating correlation images of unidirectional micro-vibration and multi-directional micro-vibration according to an exemplary embodiment.

FIG. 4 is a schematic diagram illustrating correlation images of unidirectional micro-vibration and multi-directional micro-vibration according to an exemplary embodiment.

Please refer to FIG. 1 and FIG. 4. In a correlation image 410 of unidirectional micro-vibration, it is more difficult to determine the ablation area. However, in a correlation image 420 of multi-directional micro-vibration, the ablation area may be determined.

Figure 5:
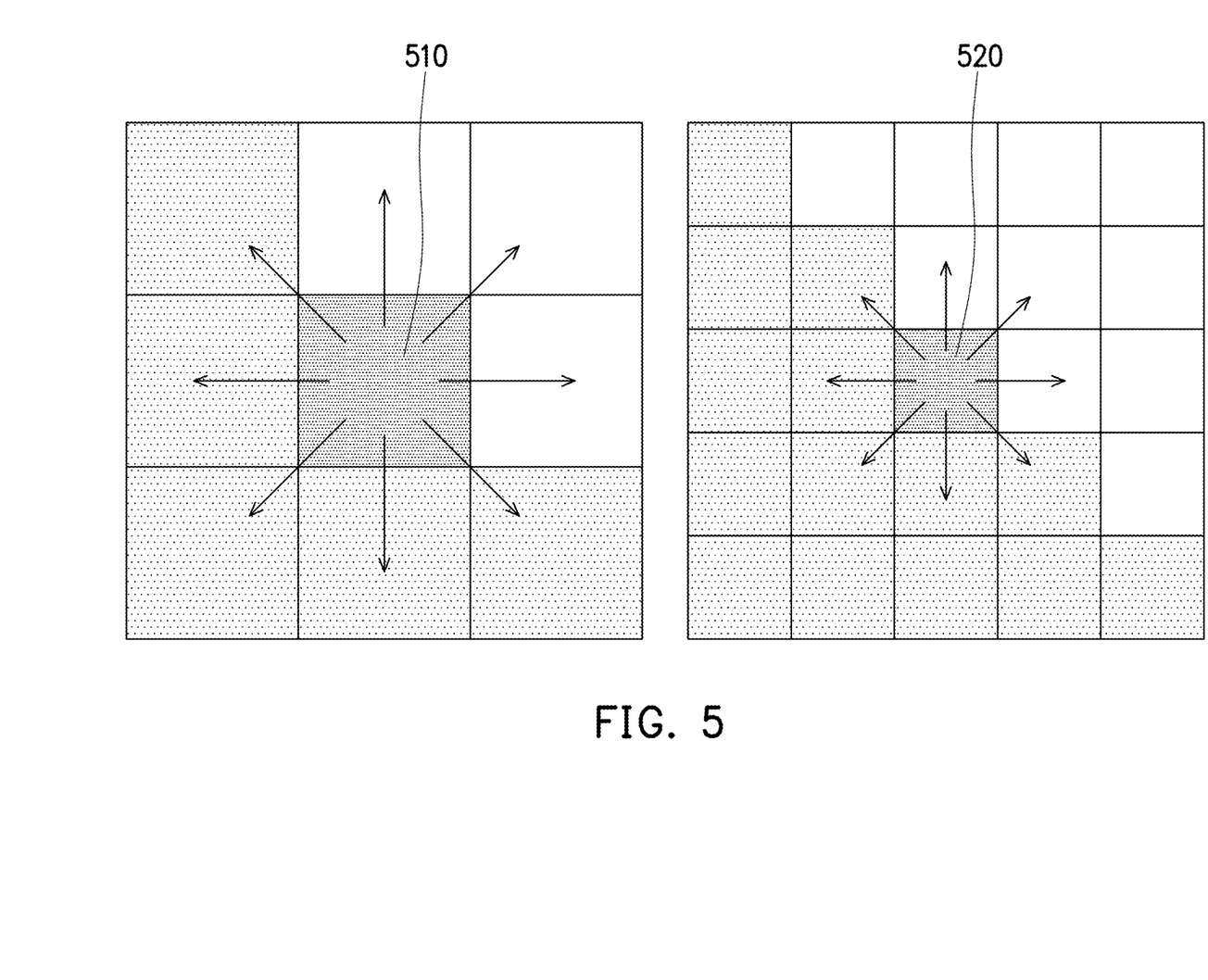
FIG. 5 is a schematic diagram of vibration directions of an electronic probe according to an exemplary embodiment.

FIG. 5 is a schematic diagram of vibration directions of an electronic probe according to an exemplary embodiment.

Please refer to FIG. 1 and FIG. 5. In an image (such as the second image) captured by the imaging apparatus 140, the vibration direction of the electronic probe 110 includes a single pixel in the pixel array of the image and more than half of the pixels surrounding the single pixel. Taking a 3×3 pixel array as an example, the vibration direction of the electronic probe 110 includes at least a pixel 510 and five surrounding pixels. Taking a 5×5 pixel array as an example, the vibration direction of the electronic probe 110 includes at least a pixel 520 and fourteen surrounding pixels (i.e., 14/24=58% of the pixels). The imaging apparatus 140 then recognizes the difference between the first image and the second image before and after the vibration, and then computes the correlation so as to generate the correlation image 210.

Please refer to FIG. 1 again. When the actuator 150 is activated, the displacement in the air of the electronic probe 110 by vibration is larger than pixel sizes of the first image and the second image. In this way, the tissue hardened by ablation will generate corresponding displacement/deformation in the second image that is distinguished from the first image and identified in the correlation image. For example, when the first image and the second image have 128 pixels arranged in an interval of 3.8 cm, the displacement of the electronic probe 110 by vibration is larger than 0.03 cm (i.e., 3.8/128=0.03), so as to ensure that the vibration is recognized in the image. On the other hand, a vibration frequency of the electronic probe 110 is larger than frames per second (FPS) of the image captured by the imaging apparatus 140. For example, when the FPS captured by the imaging apparatus 140 is 15, the vibration frequency of the electronic probe 110 is larger than 15. In this way, the imaging apparatus 140 then obtains a correct vibration image.

Figure 6:
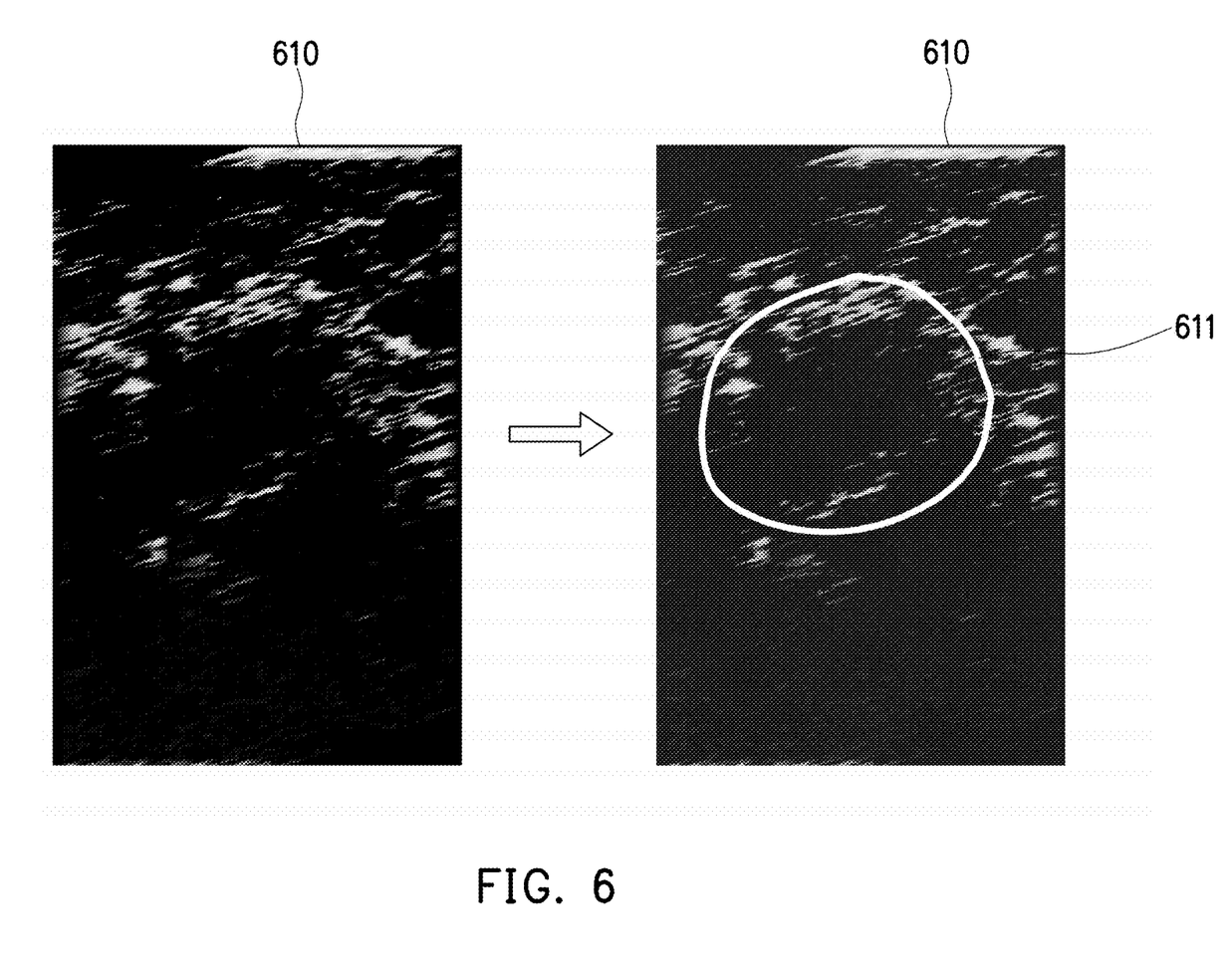
FIG. 6 is a schematic diagram of computing an ablation boundary according to an exemplary embodiment.

FIG. 6 is a schematic diagram of computing an ablation boundary according to an exemplary embodiment.

Please refer to FIG. 1 and FIG. 6. The doctor may first manually scatter points at multiple positions on a correlation image 610 using the electronic device 160. The electronic device 160 then converges the multiple positions of the manually scattered points into an ablation boundary 611 by means of a boundary detection algorithm (e.g., the SNAKE algorithm). In another embodiment, the electronic device 160 may also directly compute the ablation boundary 611 according to the correlation image 610 by the boundary detection algorithm.

Figure 7:
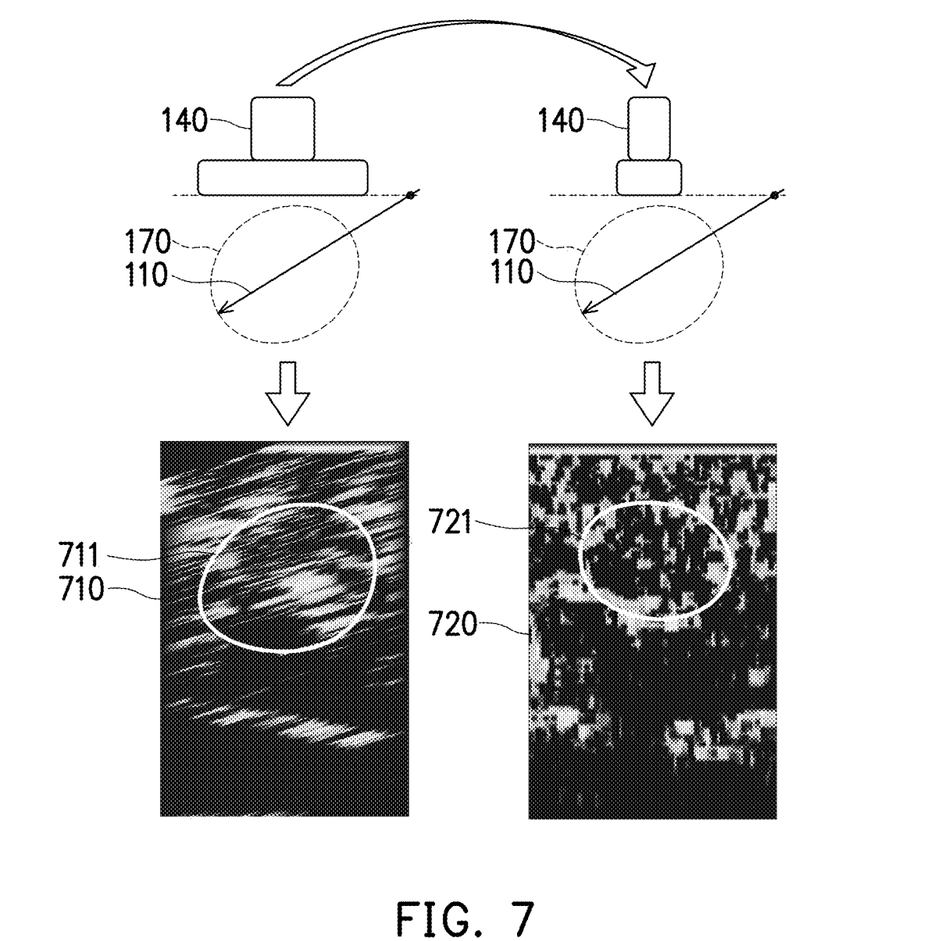
FIG. 7 is a schematic diagram of computing an ablation boundary of an imaging apparatus at different postures according to an exemplary embodiment.

FIG. 7 is a schematic diagram of computing an ablation boundary of an imaging apparatus at different postures according to an exemplary embodiment.

Please refer to FIG. 7. Some signals may be blocked by the electronic probe 110 when capturing the image at a single angle using the imaging apparatus 140, therefore in the disclosure, the imaging apparatus 140 may be configured to capture the image at two different postures (different angles). For example, a first correlation image 710 is obtained by the imaging apparatus 140 contacting the patient 120 at a first posture, and a second correlation image 720 is obtained by the imaging apparatus 140 contacting the patient 120 at a second posture. For example, the imaging apparatus 140 is rotated on the patient 120 at a predetermined angle, from the first posture to the second posture. In the present embodiment, the predetermined angle is 90 degrees. The positions and angles of the first posture and the second posture of the imaging apparatus 140 may be corrected by the sensor 111 and the sensor 141. At the first posture, the electronic device 160 obtains the first image, and the second image generated by activating the actuator 150 to vibrate the electronic probe 110, and computes the first correlation image 710 and the corresponding first ablation boundary 711 according to the first image and the second image.

In one embodiment, the imaging apparatus 140 may capture a third image including the lesion area 170 at the second posture. The actuator 150 may be activated to vibrate the electronic probe 110 and the imaging apparatus 140 may capture a fourth image including the lesion area 170 at the second posture. The electronic device 160 may compute the corresponding second correlation image 720 according to the third image and the fourth image, and compute a second ablation boundary 721 according to the second correlation image 720. The electronic device 160 may compute a first length of a first axis of the first ablation boundary 711 and compute a second length of a second axis of the second ablation boundary 721. The first ablation boundary 711 and the second ablation boundary 721 may be, for example, elliptical, and both the first axis and the second axis are elliptical long axes (or short axes). When the difference between the first length and the second length is less than a threshold value, the electronic device 160 generates an ablation boundary confirmation message. When the difference between the first length and the second length is larger than or equal to the threshold value, the first ablation boundary and/or the second ablation boundary are recomputed. In detail, the reason for the large difference between the first length and the second length may be caused by problems in the manual point scatting on the first correlation image 710 and/or the second correlation image 720. Therefore, the electronic device 160 may prompt the doctor to manually scatter points again on the first correlation image 710 and/or the second correlation image 720 and re-obtain the first converged ablation boundary 711 and/or the converged second ablation boundary 721, and then to determine whether or not an ablation range is correct according to the recomputed first ablation boundary 711 and the recomputed second ablation boundary 721.

Figure 8:
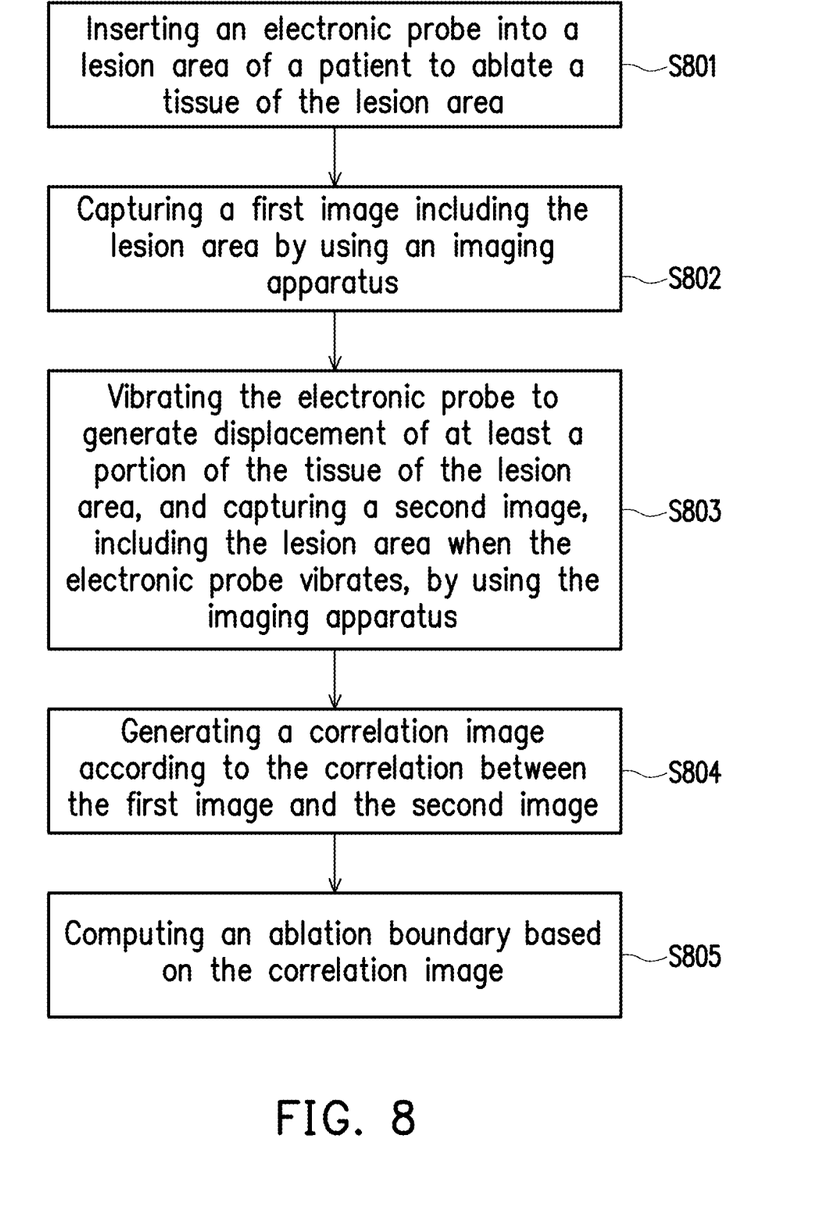
FIG. 8 is a flowchart of a tissue imaging method according to an exemplary embodiment.

FIG. 8 is a flowchart of a tissue imaging method according to an exemplary embodiment.

Please refer to FIG. 8. Step S801: inserting the electronic probe into the lesion area of the patient to ablate the tissue of the lesion area.

Step S802: capturing the first image including the lesion area by using the imaging apparatus.

Step S803: vibrating the electronic probe to generate displacement of at least a portion of the tissue in the lesion area, and capturing the second image, including the lesion area when the electronic probe vibrates, by using the imaging apparatus.

Step S804: generating the correlation image according to the correlation between the first image and the second image.

Step S805: computing the ablation boundary according to the correlation image.

An embodiment of step S805 may further include: receiving multiple input data corresponding to multiple positions in the correlation image, and converging the positions to the ablation boundary by a boundary detection algorithm.

In summary, in the tissue imaging method of the disclosure, an electronic probe is inserted into the lesion area of the patient to ablate the tissue of the lesion area, and the first image including the lesion area, and the second image, including the lesion area when the electronic probe vibrates, are captured by using the imaging apparatus. After computing the correlation between the first image and the second image to generate the correlation image, the ablation boundary according to the correlation image may be computed to confirm whether or not the lesion area is completely ablated.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A tissue imaging method, comprising:
inserting an electronic probe into a lesion area of a patient to ablate tissue of the lesion area;
capturing a first image including the lesion area by using an imaging apparatus;
vibrating the electronic probe to generate displacement of at least a portion of the tissue of the lesion area, and capturing a second image, including the lesion area when the electronic probe vibrates, by using the imaging apparatus, wherein the displacement of the electronic probe by vibration is larger than a size of a single pixel of the first image and the second image, and a vibration frequency of the electronic probe is larger than a frames per second of the image captured by the imaging apparatus;
generating a correlation image according to a correlation between the first image and the second image; and
computing an ablation boundary according to the correlation image;
wherein the electronic probe vibrates in a first direction and a second direction from an initial position, and an angle value between a first vector corresponding to the first direction and a second vector corresponding to the second direction is larger than an angle threshold value, wherein the angle value is detected by a sensor of the electronic probe and a sensor of the imaging apparatus;
wherein the angle threshold value is a value to ensure the electronic probe being able to obtain the correlation image for determining the ablation boundary.

2. The tissue imaging method according to claim 1, wherein in the second image captured by the imaging apparatus, a vibration direction of the electronic probe at least includes a pixel in a pixel array of the second image and more than half of the pixels surrounding the pixel.

3. The tissue imaging method according to claim 1, wherein a pixel value of a pixel in the correlation image represents the correlation between a corresponding pixel in the first image and a corresponding pixel in the second image.

4. The tissue imaging method according to claim 1, wherein steps of computing the ablation boundary according to the correlation image comprises: receiving a plurality of input data corresponding to a plurality of positions in the correlation image, and converging the positions to the ablation boundary by a boundary detection algorithm.

5. The tissue imaging method according to claim 1, wherein the imaging apparatus contacts the patient at a first posture to obtain the first image and the second image, and generates a first correlation image and a first ablation boundary.

6. The tissue imaging method according to claim 5, further comprising:

the imaging apparatus capturing a third image including the lesion area at a second posture, wherein the imaging apparatus is rotated on the patient at a predetermined angle, from the first posture to the second posture;
vibrating the electronic probe and capturing a fourth image, including the lesion area when the electronic probe vibrates, at the second posture by using the imaging apparatus;
generating a second correlation image according to a correlation between the third image and a fourth image; and
computing a second ablation boundary according to the second correlation image.

7. The tissue imaging method according to claim 6, further comprising:
computing a first length of a first axis of the first ablation boundary and computing a second length of a second axis of the second ablation boundary;
when a difference between the first length and the second length is less than a threshold value, generating an ablation boundary confirmation message; and
when the difference between the first length and the second length is larger than or equal to the threshold value, re-computing the first ablation boundary and/or the second ablation boundary.

8. The tissue imaging method according to claim 7, wherein the first ablation boundary and the second ablation boundary are elliptical, and both the first axis and the second axis are elliptical long axes or short axes.

* * * * *